US006983612B2

(12) United States Patent
Beyer et al.

(10) Patent No.: US 6,983,612 B2
(45) Date of Patent: Jan. 10, 2006

(54) PROCESS FOR PRODUCING PHENOTHIAZINE GRANULES

(75) Inventors: Jürgen Beyer, Frankfurt am Main (DE); Dietmar Breier, Freigericht (DE); Gunther Effenberger, Bad Vilbel (DE); Michael Roos, Waldems-Steinfischbach (DE); Jens Ruppert, Frankfurt am Main (DE); Olaf Just, Bad Homburg (DE); Detlef Wehle, Brechen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/312,019

(22) PCT Filed: Mar. 9, 2001

(86) PCT No.: PCT/EP01/02681

§ 371 (c)(1),
(2), (4) Date: Aug. 11, 2003

(87) PCT Pub. No.: WO02/02543

PCT Pub. Date: Jan. 10, 2002

(65) Prior Publication Data

US 2004/0094749 A1  May 20, 2004

(30) Foreign Application Priority Data

Jul. 1, 2000 (DE) .............................. 100 32 137

(51) Int. Cl.
*F25C 1/00* (2006.01)
*F25D 13/06* (2006.01)

(52) U.S. Cl. .................. 62/74; 62/63; 62/66

(58) Field of Classification Search .............. 62/63, 62/57, 65, 66, 67, 74; 424/489; 544/35, 544/36; 514/224.8

See application file for complete search history.

(56) References Cited

U.S. PATENT DOCUMENTS

| 3,160,630 A | 12/1964 | Vierling ................ 260/243 |
| 3,169,868 A | 2/1965 | Borden ..................... 96/90 |
| 3,235,453 A | 2/1966 | Vierling et al. ............ 167/53 |
| 3,607,993 A | 9/1971 | Tuttle ..................... 264/8 |
| 3,684,607 A | 8/1972 | Morris et al. ............. 264/13 |
| 3,912,727 A | 10/1975 | Daniels ............... 260/243 A |
| 3,951,638 A | 4/1976 | Bradley ................... 71/11 |
| 4,021,552 A | 5/1977 | Welstead, Jr. et al. ...... 424/247 |

(Continued)

FOREIGN PATENT DOCUMENTS

AU 254 331 1/1964

(Continued)

OTHER PUBLICATIONS

English abstract for DE 4338212, May 11, 1995.

(Continued)

*Primary Examiner*—Cheryl Tyler
*Assistant Examiner*—Richard L. Leung
(74) *Attorney, Agent, or Firm*—Richard P. Silverman

(57) ABSTRACT

The invention relates to a method for producing a phenothiazine granulate with a narrow particle size distribution. At least 98% pure phenothiazine in liquid form is pressed through a device provided with boreholes and a frequency is applied to said liquid phenothiazine. The liquid phenothiazine discharged through the boreholes enters a cooling medium having a temperature of between −196 and +120° C. The drops of liquid phenothiazine thus produced are brought to a temperature below melting point and are optionally solidified in another post-cooling area. Optionally, fine-grain particles or coarse-grained particles thus formed can be subsequently removed by appropriate methods. The bulk density of the obtained phenothiazine granulates ranges more particularly from 720–780 kg/m$^3$.

12 Claims, 4 Drawing Sheets

U.S. PATENT DOCUMENTS

Figure 1:
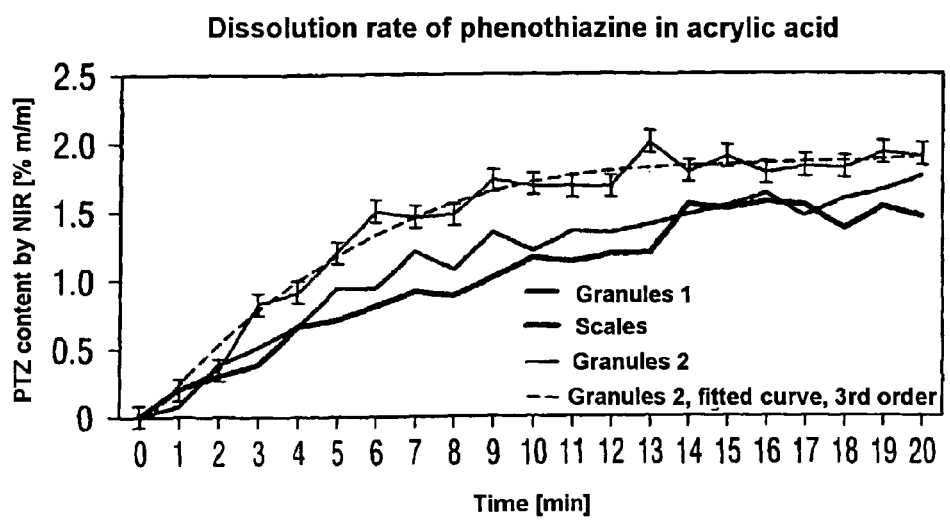

| | | | |
|---|---|---|---|
| 4,430,452 A | 2/1984 | Buysch et al. | 521/107 |
| 4,565,834 A | 1/1986 | Buysch et al. | 521/121 |
| 4,608,399 A | 8/1986 | Buysch et al. | 521/129 |
| 4,785,095 A | 11/1988 | Salomon | 544/38 |
| 4,897,436 A | 1/1990 | Buysch et al. | 524/83 |
| 5,006,284 A | 4/1991 | Gahan | 264/9 |
| 5,024,774 A | 6/1991 | Salomon | 252/47 |
| 5,321,026 A | 6/1994 | Garret et al. | 514/225.2 |
| 5,451,337 A | 9/1995 | Liu et al. | 252/102 |
| 5,772,187 A | 6/1998 | Wirodihardjo et al. | 266/241 |
| 6,284,279 B1 * | 9/2001 | Vanzin | 424/489 |

FOREIGN PATENT DOCUMENTS

| | | |
|---|---|---|
| DE | 43 38 212 | 5/1995 |
| EP | 0 070 436 | 1/1983 |
| EP | 0 275 910 | 7/1988 |
| EP | 0 277 508 | 8/1988 |
| EP | 0 499 126 | 8/1992 |
| WO | WO 99/33555 | 7/1999 |

OTHER PUBLICATIONS

Levy, Leon B., "Inhibition of acrylic acid polymerization by phenothiazine and p-methoxyphenol", Journal of Polymer Science: Polymer Chemistry Edition, vol. 23, 1985, pp. 1505-1515.

Rommps Chemie-Lexikon, 8$^{th}$ Edition, pp. 3133.

Material Safety Data Sheet for PTZ Phenothiazine, Sep. 13, 1994, Zeneca, Inc., Wilmington, DE 19897.

Zeneca Specialties, Technical Information Bulletin, "PTZ® Phenothiazine A Stablilizer For A Variety of Chemical Applications", pp. 1-12, 1998.

Gouda Jet Priller Brochure (13 pages).

Gouda Company Profile Brochure (16 pages).

* cited by examiner

Particle size distribution of phenothiazine scales

PROCESS FOR PRODUCING PHENOTHIAZINE GRANULES

The present invention relates to a process for the preparation of phenothiazine granules having improved solubility and handling properties.

Phenothiazine (2,3,5,6-dibenzo-1,4-triazine, CAS No. 92-84-2) is a starting material for thiazine dyes and sulfur dyes, an intermediate for the preparation of drugs and is furthermore used as an antioxidant for lubricating oils and engine oils, as anthelmintics (in the veterinary medicine sector), as an agent against fruit, vegetable, cereal and cotton pests and, in the largest amount, as a polymerization inhibitor for ethylenically unsaturated carboxylic acids (Ullmann, XX Edition, Vol. 18, page 259 et seq.; Römpps Chemie-Lexikon, 8th Edition, page 3133)

Phenothiazine is produced on an industrial scale by reacting diphenylamine and sulfur in the presence of catalysts. Hydrogen sulfide formed thereby is bound with sodium hydroxide solution to give sodium hydrosulfide. The crude phenothiazine formed is then purified by suitable purification methods, for example by distillation under reduced pressure or steam distillation. The melting point of pure phenothiazine is 185.5–185.9° C. and the boiling point at atmospheric pressure is 371° C.

Depending on the intended use, after preparation and purification, phenothiazine subjected to a final manufacturing step, i.e. is brought into suitable solid forms. For use as anthelmintics, phenothiazine is used, for example, in a particle size of less than 30 µm, preferably less than 20 µm (AU-B-254 331). This patent describes the preparation of phenothiazine having a specific surface area of 25.000 $cms^2/g$ by vaporizing crude or commercial phenothiazine and then condensing it in a gas stream by thorough mixing of the gas streams, phenothiazine having a purity of >95% and in the form of crystalline particles with a specific surface area of at least 25.000 $cms^2/g$ being said to be obtained. Owing to the economic advantages, AU-B-254 331 furthermore mentions the use of a fluidized bed as a preferred method for the preparation of the phenothiazine particles described. Furthermore, it is stated there that the fluidized bed consists of porous aluminum silicates or porous forms of alkali metal and alkaline earth metal carbonates or other salts, to which the phenothiazine is applied by the fluidized-bed process.

U.S. Pat. No. 3,235,453 describes further methods for the preparation of phenothiazine particles. Specifically, the comminution of precomminuted phenothiazine by means of a hammer mill and the use of micropulverizers, ball mills, air-jet mills or wet milling are mentioned.

With the object of preparing phenothiazine having a very small particle size, U.S. Pat. No. 3,235,453 describes the preparation of an improved mixture, phenothiazine being dissolved in a solvent and brought into contact with a solid and the solvent then being removed.

All stated methods have the object of preparing phenothiazine having a very small particle size (for use as anthelmintics) since the action of contact poisons is better the smaller the particle size.

For use as a polymerization inhibitor for ethylenically unsaturated carboxylic acids, phenothiazine is employed in solid form and is used, for example, in the distillation of acrylic acid in the production process on an industrial scale. Phenothiazine remains substantially in the residue of the distillation. Phenothiazine is such an effective inhibitor for acrylic acid that its use usually leads to problems in the polymerization of acrylic acid, the main field of use. For this reason and because of the dark color of phenothiazine, acrylic acid is generally inhibited using other inhibitors, e.g. hydroquinone monomethyl ether, a colorless compound (L. B. Levy, Inhibition of Acrylic Acid Polymerization by Phenothiazine and p-Methoxyphenol, Journal of Polymer Science, Polymer Chemistry Edition, Vol. 23, 1505–1515, 1985).

For metering reasons and reasons relating to simplified handling, the use of phenothiazine solutions would be entirely desirable for the use of phenothiazine as a stabilizer in the distillation of ethylenically unsaturated carboxylic acids, such as, for example, acrylic acid, but this is prevented by the poor solubility of phenothiazine in conventional solvents (in some cases substantially less than 10%), with the result that correspondingly large storage apparatuses would be required. The choice of solvents is furthermore limited by the fact that they have to be completely inert to acrylic acid and furthermore may not distill over during the distillation, since otherwise the purity of the acrylic acid would not comply with the claims (acrylic acid is generally used in polymerization processes which are sensitive to impurities).

With a few exceptions, for example the use of an approximately 6% strength solution of phenothiazine in ethyl acetate as a shortstop inhibitor for acrylic acid (this is to be understood as meaning the very rapid metering of phenothiazine as an inhibitor for the polymerization of ethylenically unsaturated carboxylic acids, for example in the case of incipient polymerization of acrylic acid without additives or on overheating of storage containers and because of polymerization as a result of a runaway reaction), phenothiazine is therefore used in solid form in the industrial production of ethylenically unsaturated carboxylic acids.

A conventional form is the preparation and use of phenothiazine in the form of scales, liquid phenothiazine, for example after purification by distillation is complete, being applied to a chilled roll and the resulting layer of solid phenothiazine being broken off the roll by means of a scraper system in the form of scales. The thickness of the scales can be controlled within certain limits; in general, scales or flakes having a thickness of from about 0.2 to 4 mm and measuring from 0.2 to 20 mm in the other two dimensions can be prepared in this manner. During the preparation of the scales themselves or during the subsequent transport in the production facility to storage means or later in corresponding transport containers to the consumer, fine dust having a particle size of <300 µm is additionally formed in amounts of up to 5% and has to be substantially removed by classical methods (for example sieving and recycling to the preparation process for phenothiazine). A low fine dust content is necessary because fine phenothiazine dust has a high tendency to form explosive mixtures in air, which is thus relevant for safety during handling of this substance.

From the description of the preparation process for solid phenothiazine, it is evident that the resulting solid particle conglomerate is inhomogeneous from the point of view that the particles have a relatively large variability of the particle size distribution within said limits, which as such are to be understood merely by way of example. In addition, fine fractions may once again be formed during transport in the production facility or during transport to the consumer as a result of poor shear stability, which fine fractions, owing to the higher dust explosion class (easier ignitability as a mixture with air, i.e. ignition at lower ignition energy which can be supplied by igniting sparks as well as by static electricity or friction), for fine dust and the higher risk of inhalation during handling of phenothiazine, necessitate increased safety and work safety precautions.

Furthermore, the dissolution behavior of phenothiazine in ethylenically unsaturated carboxylic acids is of course dependent on the particle size distribution. From the above, it follows that, depending on the transport distance or different mechanical loads, different dissolution rates are to be expected on reaching the user, which necessitates a greater monitoring effort and inclusion of time buffers during operation, for example in the dissolution process, and finally means insufficient process stability.

Improved and also better reproducible solubility behavior should be achieved by the preparation and use of phenothiazine of extremely small particle size, but this gives rise to the abovementioned safety problems and accordingly safety precautions which additionally have to be taken in respect of dust explosivity and problems relating to occupational hygiene, as well as the fact that solids having a very small particle size have only a low bulk density, which has adverse effects on the economics of transport. Furthermore, with the use of phenothiazine in the form of scales and shipping in large containers, for example in big bags having contents weighing up to 1 metric ton in practice, caking of the material is observed and the material then has to be brought into a pourable and meterable form in a time-consuming and labor-intensive manner by employing mechanical methods, such as vibration, braking or comminution by means of rods.

The object was therefore to develop a preparation process for phenothiazine which does not have said disadvantages but gives phenothiazine having a narrower particle size distribution, a smaller fine particle fraction, constant and improved solution properties and high bulk density as well as improved transport properties compared with the preparation process of the prior art and in addition is economical with respect to the preparation.

It has now surprisingly been found that the above object is achieved by a process for the preparation of phenothiazine granules having a narrow particle size distribution, phenothiazine having a purity of at least 98% in liquid form being forced through a means provided with holes and an oscillation of product-specific frequency, which supports the formation of uniform drops, being introduced into the liquid in a suitable manner. The phenothiazine emerging from the holes enters a cooling medium having a temperature of from −196° C. to +120° C., the liquid phenothiazine drops produced being brought to a temperature below the melting point and said drops being, if required, further solidified in a downstream cooling zone.

The particle diameter can be controled by various parameters. An important parameter is the diameter of the holes in the perforated plate. According to the invention, a die plate having holes with a diameter in the range of from 0.2 to 1.5 mm, preferably with a diameter in the range from 0.3 to 0.9 mm, in particular with a diameter in the range of from 0.4 mm to 0.6 mm, is suitable for forcing through the liquid phenothiazine.

Granulation apparatuses, as used, for example, for the preparation of polyethylene waxes, oxidized polyethylene, resins having a low molecular weight, atactic polypropylene, fats or alcohols or wax mixtures, can also be used for the preparation of the phenothiazine granules described.

In said granulation apparatuses, the phenothiazine to be granulated or to be pelleted, in liquid form, is forced through a perforated plate, a frequency being applied to the phenothiazine.

Usually, the resonant frequency to be applied is in the range of from 100 to 10 000 Hz, preferably in the range of from 200 to 5 000 Hz. The optimum frequency for achieving a uniform drop spectrum can be determined in a simple manner by a person skilled in the art by means of optimization experiments.

The liquid droplets formed thus formed are solidified to spherical ellipsoidal solid particles in a cooled gas stream (cooling medium). After solidification, which may be accompanied by complete or partial crystallization, which initially takes places in the outer region of the liquid droplets, complete solidification or crystallization is effected in general by a downstream cooling zone.

The surface structure as well as the porosity of the solid particle is moreover influenced by other parameters, such as, for example, the velocity of the countercurrent cooling medium and the temperature of the cooling medium.

Suitable cooling media are air, nitrogen and inert gases having a temperature in the range of from −196 to +120° C., in particular having a temperature in the range of from −40 to +100° C., preferably having a temperature in the range of from +20 to +100° C.

The velocity with which the cooling medium flows countercurrent to the phenothiazine drops is usually in the range of from 0.1 to 10 m/s, preferably in the range of from 0.5 to 5 m/s.

In a further embodiment, vaporizing nitrogen (T=>−196° C.) is used as the cooling medium. With the use of vaporizing nitrogen as a cooling medium, the height of the apparatus can be smaller than if, for example, air or an inert gas (e.g. nitrogen) at room temperature or in cooled form (from −10 to 20° C.) is used as the cooling medium.

process according to the invention makes it possible to prepare granules having a particle size distribution in the range of 300–3000 $\mu$m, in particular having a particle size distribution in the range of from 500 $\mu$m to 2 000 $\mu$m. The volume fraction of the particles having this particle size distribution is, according to the invention, at least 90%, in particular $\geq$95%, based on the total volume.

The fine particle fraction, i.e. particles having a size of <300 $\mu$m, is <3% by weight, based on the total mass, in general even less than 2% by weight, based on the total mass of granules. The fine particle fractions formed and also any resulting coarse particle fractions can be separated off by simple methods known to a person skilled in the art, for example by sieving methods.

The phenothiazine granules prepared by the process according to the invention have a smaller fine particle fraction and substantially improved solubility properties compared with phenothiazine scales prepared by the known processes or pellet material.

Furthermore, it was possible to show that the granules prepared according to the invention have better shear stability, i.e. exhibit less abrasion under mechanical stress than the abovementioned known products.

Thus, it was surprisingly found that, with the use of cooled air or cooled inert gas in the temperature range of from −10 to 20° C., in contrast to vaporizing nitrogen as a cooling medium, granules having a higher bulk density and further improved shear stability, i.e. better abrasion behavior, could be obtained in the preparation according to the invention.

The bulk densities of the granules obtained by the process according to the invention are preferably in the range of from 720 to 780 kg/m$^3$.

The granules prepared according to the invention furthermore have a substantially narrower particle size distribution. The effect of abrasion owing to a shear stress is substantially smaller in the case of the phenothiazine granules according to the invention than in the case of the phenothiazine scales prepared by the known process or pellets (cf. example 3).

The solubility behavior of the phenothiazine granules prepared can be influenced, for example, by varying the temperature of the cooling medium used. Thus, the solubility of the phenothiazine granules in acrylic acid can be substantially improved if the cooling medium has a temperature in the range of from −10 to +80° C., preferably from 0 to +60° C., during the preparation, i.e. on contact with, or on meeting, the liquid phenothiazine. The use of vaporizing nitrogen as a cooling medium results in a solubility which is lower but nevertheless higher compared with phenothiazine scales (cf. example 2).

The dissolution rate up to reaching a concentration of 1.5% in acrylic acid is in the range of from 5 to 14 minutes, in particular in the range of from 7 to 10 minutes, at room temperature in the case of granules according to the invention which have a particle size fraction of from 1 000 to 1 400 $\mu$m.

The phenothiazine granules prepared according to the invention are suitable, particularly because of their narrow particle size distribution, as additives in oils and lubricants, as a polymerization inhibitor or stabilizer or as pesticides in agriculture.

EXAMPLES

Method for determining the solubility behavior of solid phenothiazine of different forms and particle size distributions The solubility behavior is determined in comparative experiments by adding from 2 to 3% by weight, based on the total mass, of phenothiazine at room temperature to commercially available acrylic acid (Aldrich, stabilized with hydroquinone monomethyl ether). The maximum solubility of phenothiazine in acrylic acid at room temperature is about 2.8% (m/m). Thereafter, at time intervals of from 1 to 5 mm, either a.) a sample of the dispersion was taken and filtered and the phenothiazine content was determined by UV spectroscopy or b.) the phenothiazine content was determined directly by means of an NIR probe which dipped into the dispersion of phenothiazine in acrylic acid (NIRVIS universal spectrometer from Büchi having a transmission probe with 1.5 mm slit width. In order to prevent disturbances by solid particles in the measuring slit, this was closed by means of a metal screen having a mesh size of 0.18 mm).

Example 1

Determination of the Solubility Behavior of Phenothiazine Pellets, Scales and Granules According to method 1b, the solubility behavior of phenothiazine pellets (hemispheres or hemiellipsoids having a base diameter of 4–6 mm and a height of about 2–3 mm), scales (for description, see text above) and two granules prepared in different ways (granules 1, cooling medium liquid or vaporizing nitrogen; granules 2, cooling medium air or inert gas (from −10 to +20° C.)) was compared. For this purpose, in each case 1.33 g of the respective sample were added to 66 g of acrylic acid and measurements were carried out at intervals of one minute (Graph. 1).

From the solubility curves in FIG. 1, it is evident that granules 2 (cooling medium, air, temperature about 20° C.) go into solutions substantially more rapidly than scales or granules 1 (cooling medium vaporizing nitrogen) [for reasons of clarity, error bars were shown only in the case of granules 2].

Example 2

Comparison of the Solubility Behavior of Granules of Different Sieve Fractions and Different Methods of Preparation In order to exclude the possibilities that the observed differences between the granules prepared by using cooling medium close to room temperature and the granules prepared by using vaporizing nitrogen as cooling medium might be due to differences in the particle size distributions, two different sieve fractions (1000–1400 $\mu$m and 1000–1700 $\mu$m) of granules 1 and granules 2 were prepared and the solubility properties of these 4 samples were determined using method 1 b.

Figure 2:
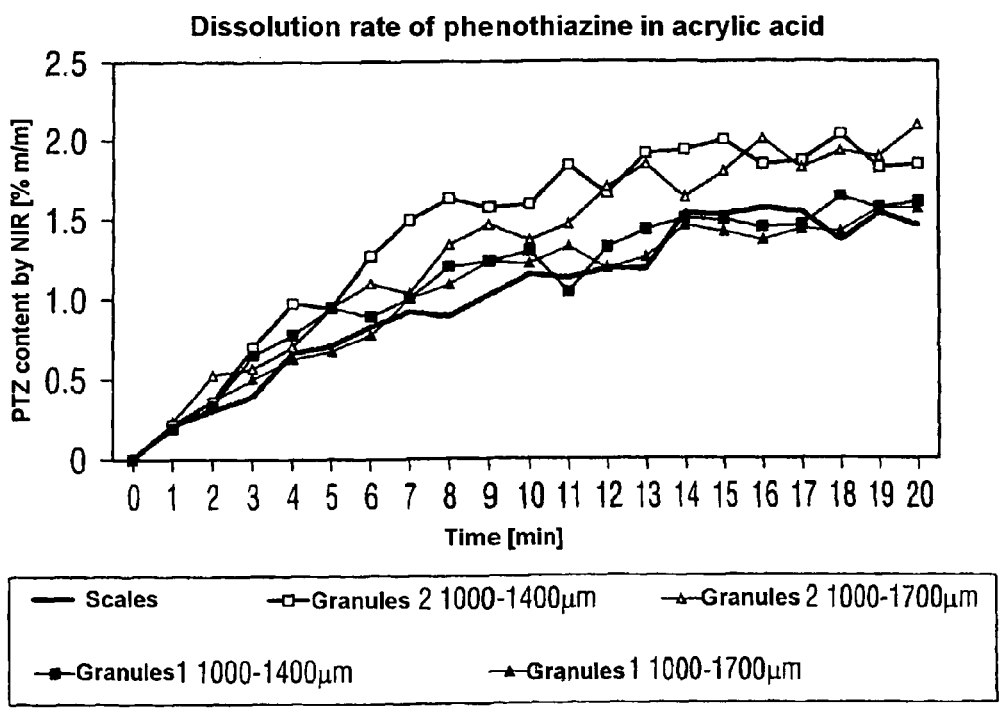

The results obtained are shown in FIG. 2:

It is clear that, in the case of both sieve fractions, but especially in the case of the sieve fraction having the particle size distribution in the range of 1000–1400 $\mu$m, granules 2 go into solutions substantially more rapidly than granules 1. The graph shows that the dissolution rate in the case of the particle size fraction 1000–1400 $\mu$m up to reaching a concentration of 1.5% is virtually twice as fast at about 7 min for granules 2 compared with about 14 min for granules 1, which constitutes a substantial application advantage in practice.

Example 3

Comparative Investigation of the Abrasion Behavior of Different Phenothiazine Particles As a measure of the shear stability of different phenothiazine samples and for simulating the abrasion behavior under transport conditions, samples were subjected to a shear stress in a shear cell of a rotational shear vessel for a period of 30 min at a direct stress of 15 kPa. The comparison of the particle size distributions before and after the measurement provides information about the abrasion behavior of the particles.

The particle size distributions are shown in the diagrams below. The cumulative undersize is shown along the ordinate and the particle size along the abscissa (logarithmic scale).

Figure 3:
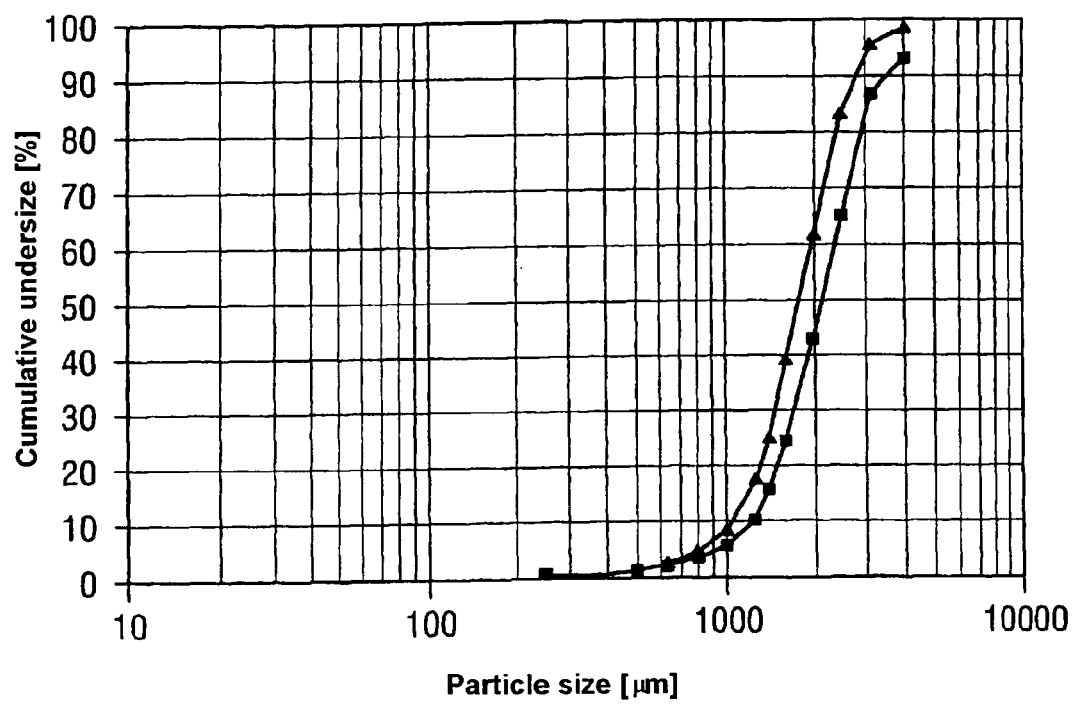

In FIG. 3 (phenothiazine scales), the solid squares represent the volume fraction of the particles up to the stated particle sizes, the plot being a cumulative plot. The particle size distribution was determined again according to the stated shear stress. That the particles are smaller throughout on average is evident from the shift of the curve to the left, toward smaller particle sizes. The graph also reveals the broad particle size distribution, which ranges from particles <200 $\mu$m to particles >4000 $\mu$m (in the unsheared state).

Figure 4:
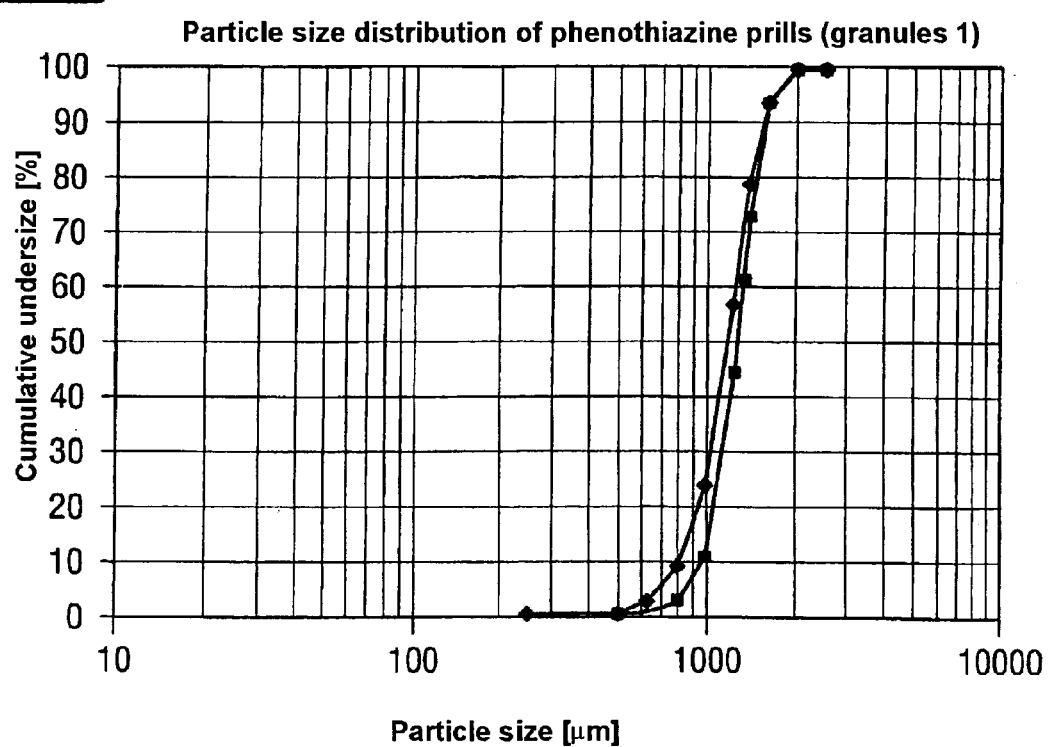
Figure 5:
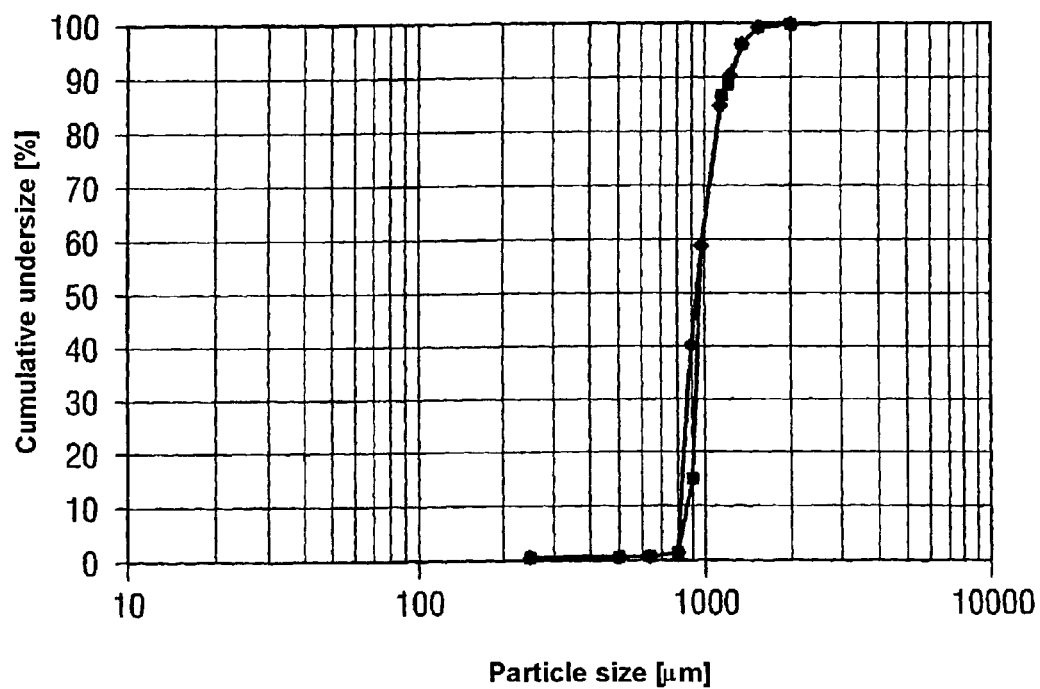

In comparison, the granules 1 and 2 (FIG. 4 and FIG. 5) have a substantially narrower particle size distribution. In the case of granules 1, finer particles were likewise formed as a result of shear stress but the effect is substantially less pronounced than in the case of the scales (smaller "hysteresis"). In the case of granules 2, the effect is once again less pronounced: here, virtually no effect of the shearing on the particle size distribution and hence on the abrasion is observable.

Example 4

Comparison of the Bulk Densities of Granules 1 and 2

The bulk densities were determined using one sample each of granules 1 and granules 2, which are characterized by the particle size distributions shown below, the bulk densities being significantly higher in the case of granules 2 at 760 kg/m³ than in the case of granules 1 at 727 kg/m³:

| Particle size | Granules 1 | Granules 2 |
| --- | --- | --- |
| 3150–4000 µm | 0.1 | <0.1 |
| 2000–3150 µm | 0.6 | 0.1 |
| 1000–2000 µm | 68.8 | 33.6 |
| 500–1000 µm | 28.1 | 65.4 |
| 250–500 µm | 2.1 | 0.9 |
| <250 µm | 0.3 | <0.1 |
| <100 µm | 0.1 | <0.1 |
| <75 µm | 0.1 | <0.1 |
| Bulk density | 727 kg/m³ | 760 kg/m³ |

What is claimed is:

1. A process for the preparation of phenothiazine granules having a narrow particle size distribution, phenothiazine having a purity of at least 98% in liquid form being forced through a means provided with holes and a frequency being applied to the liquid phenothiazine and the liquid phenothiazine emerging through the holes to form liquid phenothiazine drops and countercurrently contacting said drops with a cooling medium having a temperature in the range of from −40 to +120° C. so that the liquid phenothiazine drops thus produced are brought to a temperature below the melting point of phenothiazine to provide partially crystallized drops and said partially crystallized drops are, if required; further solidified in a downstream cooling zone to provide said phenothiazine granules.

2. The process as claimed in claim 1, wherein the means provided with holes is a die plate.

3. The process as claimed in claim 1, wherein the cooling medium has a temperature in the range of from −20 to +120° C.

4. The process as claimed in claim 1, wherein the cooling medium used is nitrogen or air.

5. The process as claimed in claim 1, wherein the cooling medium used is cooled air or cooled inert gas having a temperature in the range of from +20 to +100° C.

6. The process as claimed in claim 1, wherein the phenothiazine granules prepared have a particle size distribution in the range of from 300 to 3000 µm, the volume fraction thereof being at least 90%, based on the total volume.

7. The process as claimed in claim 1, wherein the phenothiazine granules have a fine particle fraction which is less than 3% of particles <300 µm in size.

8. The process of claim 1, wherein the phenothiazine granules have a fine particle fraction which is less than 2% of particles <300 µm in size.

9. The process as claimed in claim 1, wherein any fine particle fractions or coarse particle fractions formed are removed by suitable methods.

10. The process as claimed in claim 1, wherein a bulk density of the phenothiazine granules obtained is in the range of from 720 to 780 kg/m³.

11. The process as claimed in claim 1, wherein the phenothiazine granules have a dissolution rate, in acrylic acid, of from 5 to 14 minutes to reach a concentration of 1.5%.

12. A process for the preparation of phenothiazine granules having a narrow particle size distribution, said process comprising:

a) forcing a molten liquid phenothiazine having a purity of at least 98% through a perforated plate having holes and applying a frequency to said liquid phenothiazine to provide liquid phenothiazine drops emerging through the holes;

b) passing the liquid phenothiazine drops to a first cooling zone wherein a cooing medium flowing countercurrently at a velocity of 0.5 to 5 m/s to said drops contacts the liquid phenothiazine drops, said cooling medium having a temperature in the range of from −20 to +100° C. to cool said liquid phenothiazine drops to form phenothiazine granules, wherein at least 95 volume percent of said phenothiazine granules having a particle size distribution in the range of from 500 to 2000 µm, said phenothiazine granules having a dissolution rate in acrylic acid of between 5 to 14 minutes to reach a concentration of 1.5%, and, c) optionally; further cooling said phenothiazine granules in a downstream cooling zone.

* * * * *